United States Patent [19]

Ouchi

[11] 4,436,087
[45] Mar. 13, 1984

[54] BIOPTIC INSTRUMENT

[75] Inventor: Teruo Ouchi, Saitama, Japan

[73] Assignee: Kabushiki Kaisha Medos Kenkyusho, Tokyo, Japan

[21] Appl. No.: 967,949

[22] Filed: Dec. 11, 1978

[30] Foreign Application Priority Data

| Dec. 11, 1977 | [JP] | Japan | 52-148461 |
| Dec. 11, 1977 | [JP] | Japan | 52-166057[U] |
| Dec. 24, 1977 | [JP] | Japan | 52-155830 |
| Jan. 14, 1978 | [JP] | Japan | 53-2905[U] |
| Feb. 22, 1978 | [JP] | Japan | 53-21662[U] |
| Dec. 11, 1978 | [JP] | Japan | 53-2904[U] |

[51] Int. Cl.$^3$ .............................................. A61B 1/12
[52] U.S. Cl. ............................................................... 128/6
[58] Field of Search ........................................ 128/3–8; 356/241; 350/96.26

[56] References Cited

U.S. PATENT DOCUMENTS

| 3,561,432 | 2/1971 | Yannaki et al. | 128/6 |
| 3,896,793 | 7/1975 | Mitsui et al. | 128/6 |
| 3,903,877 | 9/1975 | Terada | 128/6 |
| 3,915,157 | 10/1975 | Mitsui | 128/6 |
| 3,924,608 | 12/1975 | Mitsui | 128/6 |
| 3,980,078 | 9/1976 | Tominaga | 128/4 |

FOREIGN PATENT DOCUMENTS

| 50-22694 | 3/1975 | Japan | 128/6 |
| 50-20489 | 7/1975 | Japan | 128/6 |
| 51-53789 | 4/1976 | Japan | 128/6 |

*Primary Examiner*—Michael H. Thaler
*Attorney, Agent, or Firm*—Sughrue, Mion, Zinn, Macpeak, and Seas

[57] ABSTRACT

A direction changing device for a bioptic instrument having a protrusion provided at the top opening edge of an insertion passage into which a bioptic member or the like of an endoscope is inserted. The top opening edge is positioned in the vicinity of an objective lens of the endoscope or before the objective lens. The protrusion serves as a fulcrum to bend a pipe of bioptic instrument.

A depressing member is located adjacent the protrusion to deflect an element of the instrument over the protrusion.

The inserted member may be a device for taking samples or a fluid injection system. The instrument body may have a hood attached to the outer end with a direction changing protrusion on it. The hood may be rotatable relative to the instrument body. Deflection of the sample device of fluid stream is accomplished by positioning the deflection member relative to the passage in the instrument. A valve may be employed to seal the passage from contaminating elements. The deflecting member may be stationary or pivoted on the body or the hood and can be remotely actuated. It may be flexible or solid and be annular or a protrusion. The deflecting member can also positively engage the sample taking device and it may be arranged for pivotal movement.

7 Claims, 41 Drawing Figures

F I G. 5
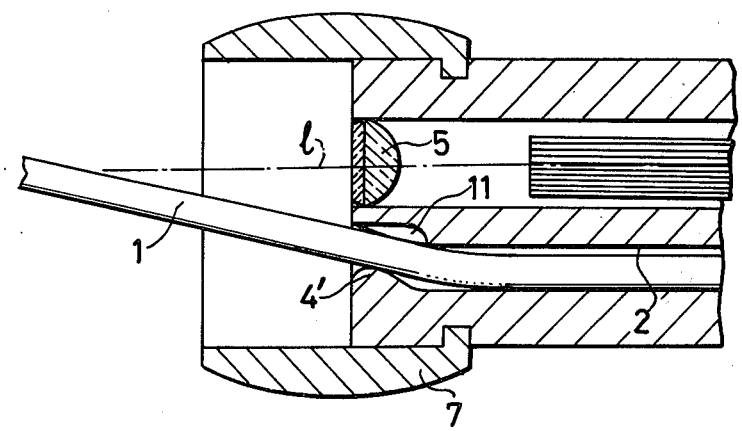
F I G. 6
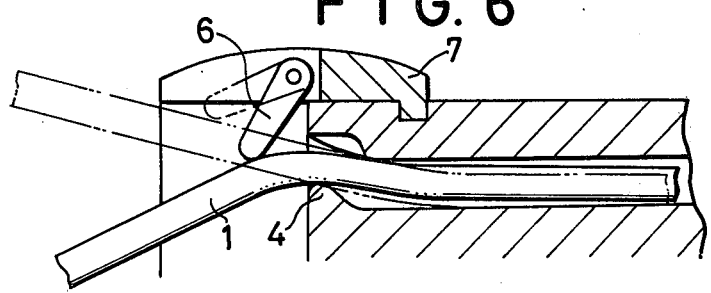
F I G. 7
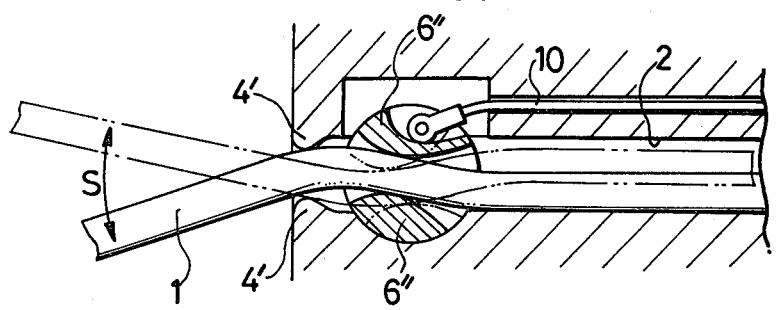

F I G. 16
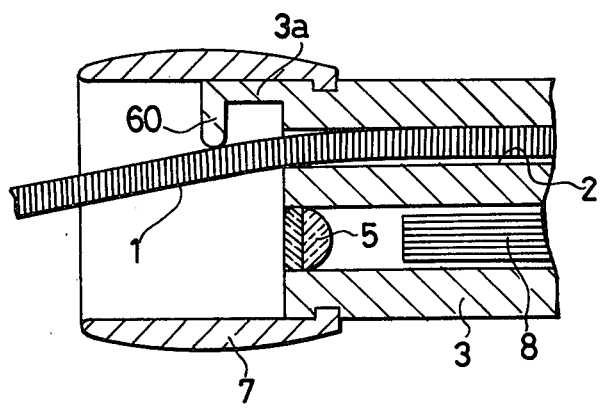
F I G. 17
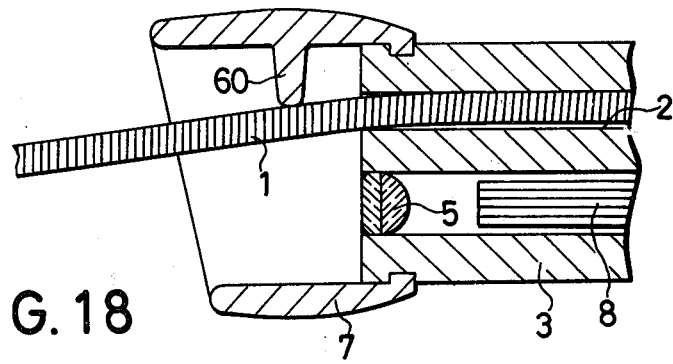
F I G. 18
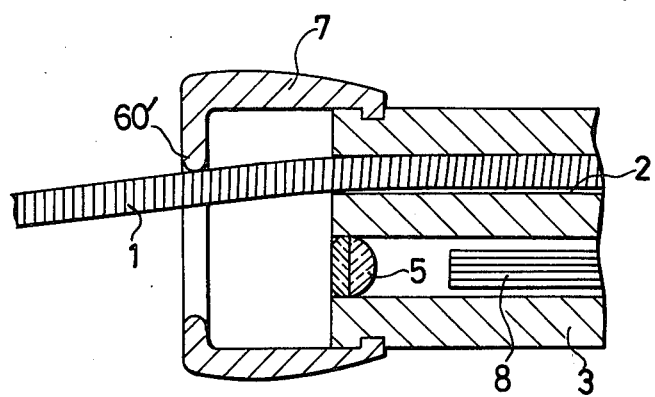

BIOPTIC INSTRUMENT

BACKGROUND OF THE INVENTION

This invention relates to a direction changing device for leading the direction of extending a bioptic instrument such as forceps to an aimed position in the field of vision for observation.

As is well known in the art, an endoscope such as a gastroscope or a bronchoscope comprises an optical system for observing a portion of the body, a bioptic instrument such as forceps for taking a sample from the body and other auxiliary devices such as for instance a device for supplying and discharging water or air. Accordingly, passages for these devices are incorporated in a flexible pipe extending from the portion of the body to be examined to the manual operating section of the endoscope. Opening and working sections for these devices are arranged in the top portion of the flexible pipe, which reaches the portion of the body to be examined.

For instance, the objective lens of an observing optical system, especially the viewing optical system and the opening of the passage for the bioptic instrument are juxtaposed in the end face of the flexible tube. Therefore, the functioning ranges, that is, the field of vision of the optical system and the region of a portion of the body to be examined to which the bioptic instrument can extend, of these devices are not in coincidence with one other. Thus, taking a sample from the portion of the body under examination in the periphery of the field of vision for observation is sometimes outside the range of the bioptic instrument, which makes it difficult to perform such operation.

Recently, a variety of devices have been proposed for allowing the working region of the bioptic instrument to approach the central region of the field of vision for observation. For instance, a device has been proposed in which an operating section is incorporated in the end portion of a flexible pipe. The operating section functions to incline the field of vision of the observing optical system towards the side of extension of the bioptic instrument with respect to the end face of the flexible tube and to deflect the pipe of the bioptic instrument to a plane which crosses the field of vision. The concept is disclosed in Japanese Utility Model Laid-Open No. 20489/1975.

A conventional technique of changing the direction of the end portion of the pipe of a bioptic instrument is disclosed by Japanese Utility Model Laid-Open Nos. 20489/1975 and 22694/1975 and Japanese Utility Model Application Publication No. 53789/1976. In these systems an operating pipe into which the pipe of the bioptic instrument is inserted is provided in the end portion of the flexible pipe and the operating pipe is deflected manually to change the direction of the pipe of the bioptic instrument.

A conventional direction changing device of this type is incorporated in the metal part provided at the end portion of the flexible tube, and therefore a larger part of the end portion of the flexible tube is occupied by the device. Accordingly, devices incorporated in the the flexible tube, i.e., devices built in the endoscope are limited. Furthermore, the field of vision of the observing optical system is apt to be narrowed by the shape of the direction changing device. In addition, the conventional direction changing device is disadvantageous in that it is impossible to increase the direction changing angle.

SUMMARY OF INVENTION

Accordingly, an object of the invention is to provide a direction changing device in which the volume of members for changing the direction of a bioptic instrument incorporated in the end portion of an endoscope is minimized by simplifying the mechanism.

Another object of this invention is to provide a direction changing device for a bioptic instrument in which the direction changing angle is larger than in prior art devices.

Still another object of this invention is to provide a direction changing device for a bioptic instrument that is reliable, easy to use and provides improved performance over prior art devices.

These another objects of this invention are accomplished by means of a novel endoscopic instrument having a protrusion provided adjacent the top opening edge of an insertion passage.

A bioptic instrument or the like of an endoscope is inserted or in the vicinity of said top opening edge and the top opening edge is positioned in the vicinity of an objective lens of the endoscope or preceding the objective lens. The protrusion serves as a fulcrum to bend a pipe of said bioptic instrument.

This invention also allows the use of a fluid stream to be injected into the cavity and selectively deflected for purposes of cleaning either the area under examination or the optics of the endoscope. The fluid stream is deflected by means of a protrusion placed in either the hood on an extension of the hollow insertable body. In the situation where a hood is employed, the orientation of the hood, and therefore the deflecting member when attached thereto can be changed relative to the ejected stream or extending instrument. The hood may be driven remotely or preset in a particular position by means of notches.

The deflecting member may also be arranged for pivotal movement either by making it flexible or having a pulling element to move the member. In the case where no protrusion is used on the opening edge, deflection takes place over the edge itself. Also, a check valve member may be used to seal any openings in the opening edge to prevent back flow of contaminating elements into the endoscope passages.

This invention will be described with reference to the accompanying drawings and the description of the preferred embodiment that follows.

BRIEF DESCRIPTION OF THE DRAWINGS

FIG. 5 is a sectional view of a third example of the preferred embodiment of this invention;

FIG. 6 is a sectional view of a fourth example of the first preferred embodiment of this invention;

FIG. 7 is a sectional view of a fifth example of the first preferred embodiment of this invention;

FIG. 16 is a sectional view of a first example of a third preferred embodiment according to this invention employing a protrusion mounted on an extension of the hollow member;

FIG. 17 is a sectional view of a second example of the third preferred embodiment using a protrusion mounted on the hood;

FIG. 18 is a sectional view of a third example of the third preferred embodiment using an annular protrusion on the hood;

DESCRIPTION OF THE PREFERRED EMBODIMENTS

A first preferred embodiment of this invention will now be described with reference to the accompanying drawings.

FIGS. 1(A) through (E) are diagrams for a description of the principle of the direction changing device according to this invention. As shown in FIG. 1(A), the end portion 3 of an endoscope is provided with a passage 2 into which the pipe 1 of a bioptic instrument is inserted. A protrusion 4 extending towards the passage is provided at the opening of the passage. Accordingly, the pipe 1 is deflected in the direction n from the centerline direction m in which the pipe in the conventional passage is extended, because the protrusion 4 serves as a fulcrum for bending the pipe 1. The protrusion 4 may be provided by curving the opening portion of the passage as shown in FIG. 1(B).

If a bending force W is applied to the pipe 1 of the instrument construced as in FIG. 1(A) as shown in FIG. 1(C), then the pipe 1 is bent in the opposite direction n'. That is, the pipe will be deflected over the protrusion 4.

If bending forces Wa and Wb are applied to two points of the pipe 1 before and after the protrusion 4 as shown in FIG. 1(D) then the pipe 1 is bent respectively in the direction na and nb, thus changing its direction. In this case, the bending angle of the direction nb is larger than that of the direction n of FIG. 1(A) mentioned above.

In the case of FIG. 1(E) an annular protrusion 4' is provided at the opening of the passage. In this case, if bending forces Wc and Wd are applied to a point of the pipe, located behind the protrusion 4', or inside the passage, the pipe 1 can be bent in the directions nc and nd.

Figure 2:
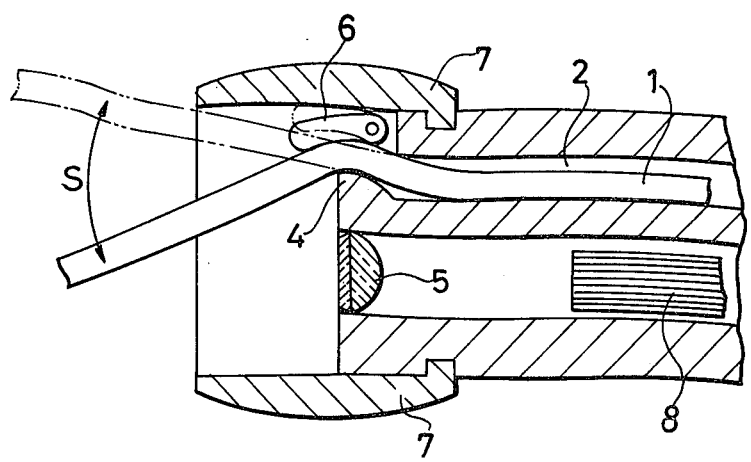
FIG. 2 is a sectional view of a first example of the first preferred embodiment of this invention using a protrusion on the opening edge as a deflecting point.

Referring now to FIG. 2 a sectional view shows the essential parts of a first example of one preferred embodiment of the device according to the invention. In this device, the opening of an insertion passage 2 is provided in alignment with the objective side surface of an objective lens 5 of an observing optical system. A protrusion 4 is provided at the opening, and a depressing piece 6 is pivotally mounted on the pipe wall at the edge of the opening opposite to the edge of the opening where the protrusion 4 is provided. The device further comprises an annular hood 7, and a light guide 8 for the observing optical system.

Figure 3:
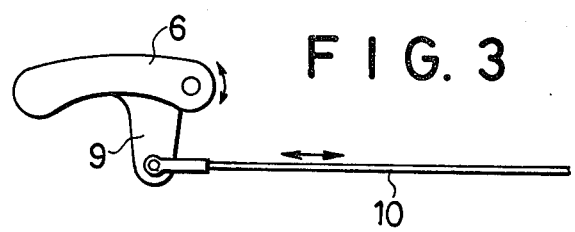
FIG. 3 is a schematic side view showing the depressing piece of FIG. 2.

The depressing piece 6, as shown in FIG. 3, is shaped so that its one end portion can depress a portion of the pipe extending over the protrusion 4, against the protrusion. For this purpose, the depressing piece 6 has an extension 9 which is connected to one end of a pulling string 10 which is connected to the manual operating section of the endoscope. The depressing piece 6 is therefore shaped like a pawl, pivoted about the pivot point coupled to the pipe wall for movement as shown by the arrows in FIG. 3.

Figure 4:
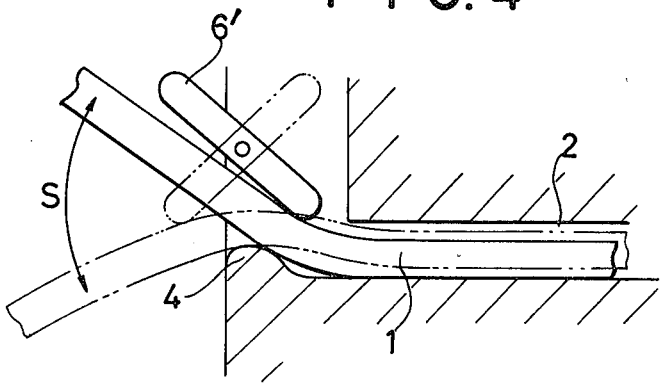
FIG. 4 is a sectional view of second example of the first preferred embodiment of this invention.

FIG. 4 is a sectional view showing the essential parts of a second example of the first preferred embodiment of the device according to the invention, in which those components which have been previously described with reference to FIG. 2 are similarly numbered. In this embodiment, a depressing piece 6' is pivoted at its middle point so that it can rotate in a circular pattern. That is, in this embodiment, both end portions of the depressing piece 6' can alternately depress the pipe 2 against the protrusion 4. As in the FIG. 2 embodiment, the depressing piece 6' has an extension connected to the pulling string (not shown) so that the depressing piece is swung by operating the pulling string.

FIG. 5 is a sectional view showing the essential components of a third example of the preferred embodiment of the device according to the invention. In this embodiment, the end portion of the insertion passage 2 is bent towards the optical axis 1 of the observing optical system in such a manner that the pipe of a forceps is extended by means of a protrusion 4' provided at the opening of the insertion passage 2, in a direction intersecting the optical axis 1. In FIG. 5, reference numeral 11 is a relief section for the pipe 1, which is formed by cutting a portion of the opening edge opposite to the opening edge where the protrusion 4' is located. In this embodiment, the point where the pipe 1 intersects the optical axis 1 is in a range that the forceps at the end of the pipe 1 is from 5 to 50 mm away from the object side surface of the objective lens 5 in the case of a bronchoscope. It is in a range so that the forceps is spaced 10 to 150 mm from the object side surface of the objective lens 5 in the case of a gastroscope.

FIG. 6 is also a sectional view showing the essential parts of a fourth example of the first preferred embodiment of a device according to the invention. In this example, the depressing piece 6 is pivotally mounted on the hood 7. This is contrasted to the FIG. 2 embodiment where the pivot point is located on the body of the pipe itself.

FIG. 7 is a sectional view showing the essential parts of a fifth example of the first preferred embodiment according to the invention. In this example, an annular protrusion 4' is formed along the edge of the opening of an insertion passage 2, and a depressing piece 6" is provided near the opening of the passage 2. The depressing piece 6" is shaped so that it can clamp both sides of the pipe 1. Since is only necessary that this depressing piece 6" depress one point of the pipe 1 inserted into the passage 2, it is unnecessary to shape it as a cylinder into which the pipe 1 is inserted. That is, it may be formed as a swinging member having a clamping section.

In the above described examples, the opening edge of the insertion passage 2 or the protrusion provided at that location serves as the fulcrum to bend the pipe 1. Therefore, it is preferable that the fulcrum be positioned in the same plane as that of the object side surface of the objective lens. Alternatively, it should be positioned before the plane so that it will not obstruct changing the direction of the pipe 1 and it may provide a large swinging angle thereof.

Figure 1:
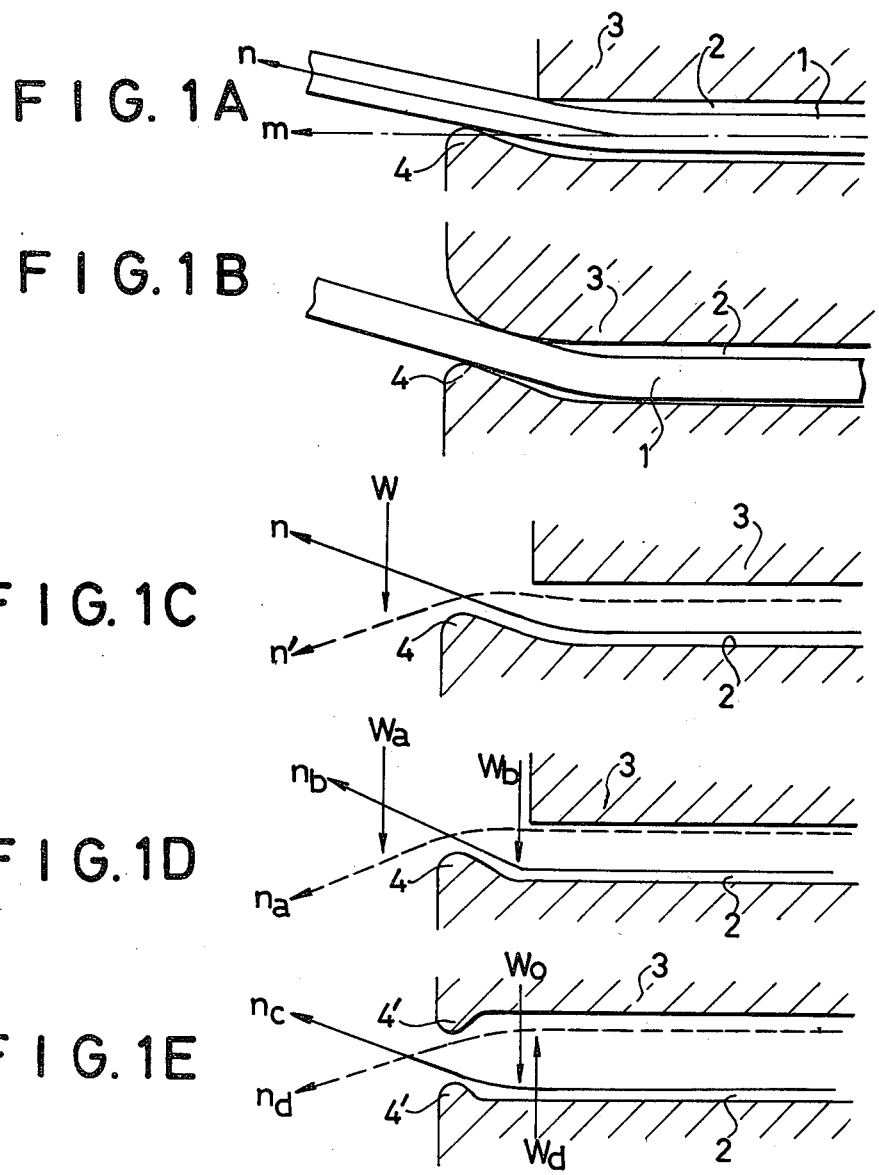
FIGS. 1(A–E) are schematic diagrams showing the operative principles of this invention.

According to the first embodiment and the examples thereof of this invention, as is apparent from the principle described with reference to FIG. 1, the pipe of the bioptic instrument is bent by being depressed by the protrusion 4 or 4' provided in the vicinity of the opening of the passage 2. The bending of the pipe 1 can be predicted from the diameter of the passage 2, the diameter of the pipe 1 inserted into the passage 2, the elasticity of the pipe 1, and the height of the protrusion 4 or 4'. Therefore, if the height of the protrusion 4 or 4' is preset by taking these bending factors into consideration, the pipe 1 can be bent as required, that is, the forceps at the end of the pipe 1 can be extended to the most effective position in operation.

In the case where the direction of the pipe is changed only by the protrusion 4 or 4', the direction change is limited to the direction in which the end of the pipe 1 is directed towards the center of the field of vision of the observing optical system. This is best shown, for instance in the example shown in FIG. 5. However, in the situation where the protrusion 4 is used in combination with the depressing piece 6, as shown in FIG. 2, the top end of the pipe 1 is directed towards the periphery of of the field of vision for observation by means of the protrusion 4. The depressing piece 6 is arranged so that, it depresses the pipe 1, acting against the change of direction of the pipe 1 caused by the protrusion 4. Thus, the direction of the pipe 1 can be changed in a wide angular range S (FIG. 2) by controlling the movement of the depressing piece 6.

In the example shown in FIG. 4, the pipe 1 can be depressed at a point behind the protrusion 4, and accordingly it can be greatly bent with its outer wall supported by the protrusion as the fulcrum. In this case, the angular range S in which the direction of the pipe 1 can be changed is further increased.

As shown in FIG. 6, bending can also be readily achieved by pivotally mounting the depressing piece 6 on the hood 7. In this case, no particular space is necessary for providing the depressing piece 6 in the top metal part of the flexible tube. Therefore, the limitation to the use of other instruments of the endoscope is eliminated. The manufacture of the direction changing device can be readily achieved without special tooling or the like.

In the case where it is possible to incorporate the depressing piece 6" in the top metal part of the flexible pipe, the direction changing device can be formed as shown in FIG. 7. In this case, the direction of the pipe 1 can be changed as desired by the protrusion 4 formed at the opening edge of the insertion passage and the clamping position of the depressing piece 6". In this example, the direction of the pipe 1 is changed depending on the positional relations between the protrusion 4 and the clamping point of the depressing piece 6". Accordingly the angular range S for changing the direction of the pipe 1 is the largest of all the examples, and the direction of the pipe can be smoothly changed.

As is apparent from the above description, the direction changing device according preferred embodiment to the invention is obtained merely by providing the protrusion at the opening of the insertion passage of a bioptic instrument or the like, and therefore the construction of the direction changing device is very simple. The direction of the pipe of forceps, for instance, protruding through the insertion passage can be changed as desired with the protrusion employed as the fulcrum, so that the forceps reaches the central region of the field of vision for observation. Thus, a bioptic instrument or the like can be readily operated under observation.

In the direction changing device, the provision of the depressing of the direction changing range of a bioptic instrument and accordingly the direction of the pipe can be manually changed as required in the wide direction changing range. Thus, a bioptic instrument or the like can be more positively operated. Naturally, in the case of the direction changing device in which only the protrusion is formed, the space occupied by the device is extremely small in the top end portion of the endoscope. Also in the case of the direction changing device in which the depressing piece is provided in combination with the protrusion, the space occupied by the device is also very small. Unlike the cylindrical member or the like of the conventional device into which a part of the pipe is inserted for changing the direction of the pipe, the depressing piece here is not bulky, that is, it is smaller in volume and its movement range for depression is small. Accordingly, the outside diameter of the top end portion of an endoscope provided with the device according to first preferred embodiment of the invention is much smaller than that of an endoscope equipped with the conventional device. Therefore the endoscope provided with the device according to the invention can be readily inserted into a portion of the body to be examined with only a small incision.

In the situation where the outside diameter of the top end portion of an endoscope equipped with the device of this invention is permitted to be equal to that of an endoscope with the conventional device, it is possible to increase the number of image fibers, for instance, incorporated in the endoscope. This will enlarge the observing image to improve the diagonostic efficiency. Furthermore, if the number of light guide fibers is increased, it is possible to obtain a bright observing image and to take photographs of a portion of the body to be examined.

The direction changing function of the device according to the invention is performed by the utilization of a fulcrum. Furthermore, since the fulcrum is positioned in the vicinity of the opening of the insertion passage, no structural obstruction is provided in the direction changing region thereof and therefore a large direction changing angle can be obtained. Accordingly, a bioptic instrument or the like can be protruded under a condition where it is very close to the objective lens, and therefore a stable operation can be effected with a short observation distance.

Figure 8:
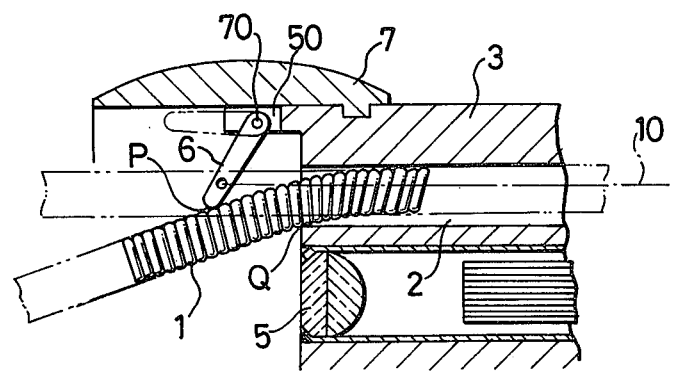
FIG. 8 is a sectional view of a second preferred embodiment of this invention using a deflecting member located beyond the opening edge.

Referring now to FIG. 8, a sectional view shows the essential components of a second preferred embodiment of the direction changing device according to this invention. The pipe of a bioptic instrument or the like is inserted into an insertion passage 2 formed in the top metal part 3 of an endoscope. The opening edge of the passage 2 and an objective lens 5 of an observing optical system are arranged in the end face of the elongate member 3. An extension 50 protrudes from a portion of the edge of the member 3, which is near the insertion passage 2. That is, the extension 50 extends from the end face of the member 3. One end portion of a depressing member 6 is pivotally mounted on a pivot shaft 70 embedded in the extension 50. The extension 50 is disposed inside the hood 7.

More specifically, the depressing member 6 is arranged so that its free end portion abuts against the outer wall of the pipe 1 extended from the passage 2 whereby the pipe 1 is deflected towards the objective lens 5. In this embodiment the protrusion at point Q is eliminated and the depressing member is disposed beyond the opening edge. In FIG. 8, reference numeral 10 designates a pulling string tied with the depressing member 6, and reference characters P and Q designate the point of application and a fulcrum, respectively.

Figure 9:
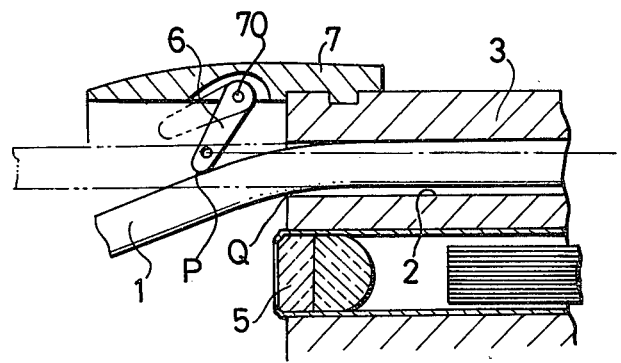
FIG. 9 is a sectional view of a second example of the second preferred embodiment of this invention.

FIG. 9 is a sectional view showing the essential components of a second example of the device according to the second preferred embodiment of this invention. In this example, the depressing member 6 is pivotally mounted (as indicated by 70) on a part of the inner wall of the hood 7.

In this embodiment the pivotal mounting is disposed in a recess in the hood.

A variation of FIG. 9 is shown in FIGS. 10-13 for deflections air or water from a supply device so that the observation surface of a portion of the body to be examined can be selectively cleaned.

When the end portion of an endoscope is inserted into the body for observing a portion of the body to be examined, or during the observation, body fluid or mucus is liable to stick on the end portion of the endoscope. Therefore, it is necessary to clean it to maintain the viewing function of the observing optical system.

For this purpose, an air or water supplying passage is usually provided in the endoscope, so that the aforementioned cleaning is effectuated with air or water supplied through the passage. In order to more effectively achieve this cleaning, a device has been proposed in which the flow-course of air or water can be directed towards the endoscope window provided in the top end portion of the endoscope.

However, these conventional devices operate merely to put aside the material stuck on the end portion of the endoscope with water supplied through the above-described passage, and accordingly it is impossible to sufficiently remove the material from the end portion of the endoscope. In the case where air or water is ejected towards the endoscope window with a nozzle, the material stuck thereon can be sufficiently removed. However, since the air or water thus ejected is applied only to a small area in the end portion of the endoscope, for instance, the front surface of the objective lens of the observing optical system, it is rather difficult to effectively remove the foreign material from the end face of a light guide adapted to irradiate the portion of the body to be examined. Also sometimes the small hole in the nozzle is clogged up with the foreign matter.

Accordingly, this variation of the deflection device of FIG. 9 can be modified to provide an air or water supplying device in an endoscope, which is capable of not only cleaning the end portion of the endoscope but also cleaning the observation surface of a portion of the body to be examined.

Figure 10:
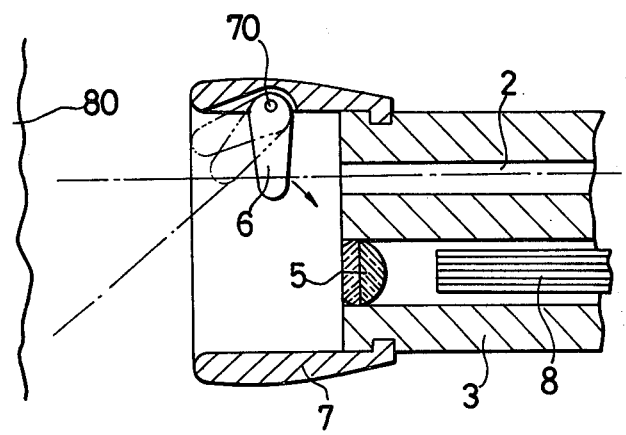
FIG. 10 is a sectional view showing a variation of the second example for use in cleaning the optics or area to be observed.
Figure 12:
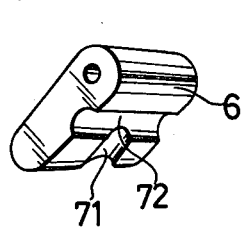
FIG. 12 is a perspective view of a second type of deflection device having orthogonal flow directing channels.

FIG. 10 is a sectional view showing the essential parts of one variation of the device according to the second example of this preferred embodiment. An objective lens 5 of an observing optical system is provided in the top end portion of the hollow member 3 connected to the end portion of an endoscope, and it is optically coupled through an image guide fiber 8 to an observing section provided at the base of the endoscope. In FIG. 10, reference numeral 2 designates an air and water supplying passage provided in parallel with the path of the fiber 8, and the outlet of the air and water supplying passage 2 is provided in the vicinity of the opening of the objective lens 5. The end face of a light guide for observation (not shown) and the opening of an air and water discharging passage are provided in the elongate member 3. The passage 2 is the same as used in FIG. 9 for insertion of member 1 through the endoscope.

In FIG. 10, reference numeral 7 designates a top hood fitted to the hollow member 3. One end portion of a flow-course switching piece 6 in the form of a plate is pivotally secured to a portion of the inner wall of the top hood 7. As shown in FIG. 10 the pivot point 70 is located in a recess of the hood. More specifically, the switching piece 6 is operated in a switching mode so that its free end portion is protracted to the flow-course of the air or water jetted from the opening of the passage 2 and is retracted therefrom as required. That is, the switching piece 6 is swung around its pivot shaft 70 embedded in the inner wall of the hood.

Figure 13:
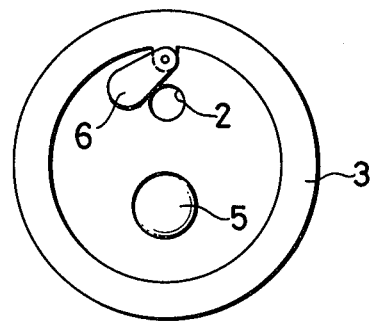
FIG. 13 is an end view showing an alternative mounting of the deflection member perpendicular to the flow opening.

The switching piece 6 may be designed as shown in FIG. 4 so that it is swung about an axis perpendicular to the flow of air or water and also in a direction perpendicular to the flow-course of air or water. Alternately, the switching piece 6 may be pivotally mounted on its pivot shaft which is embedded in an edge member extended from the hollow member 3 wherein the pivotting axis is parallel to the direction of fluid flow and the piece 6 is swung in a direction perpendicular to fluid flow, as shown in FIG. 13.

The switching piece 6 may be designed so that the switching piece 6, after switched, is maintained at its preselected position by means of a click stop mechanism or a screw stop mechanism provided at the pivot section of the switching piece 6. Alternatively, the switching piece 6 may be designed so that its switching positions can be selectively obtained by manually operating a pulling string or an operating rod which extends to the manual operating section of the endoscope. This technique is shown in FIG. 9.

Figure 11:
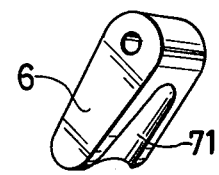
FIG. 11 is a perspective view of one type of deflection device having a flow directing channel.

When the switching piece 6 is projected into the flow-course, its side surface receives the air or water ejected out of the opening of the passage 2. As a result the air or water is directed, as indicated by the arrow, to cover the large area in the end face of the hollow member 3. In the case where it is necessary to give directivity to the flow of air or water towards the end face of the member 3, this can be satisfied effectively by cutting a flow-course guide groove 71 or 72 in the side surface of the switching piece 6 as indicated in FIG. 11 or 4.

When the cutting piece 6 is retracted from the flow-course as indicated by the dotted line in FIG. 10, the air or water flowing from the passage 4 is supplied direct in a straight line to the observation surface of a portion of the body to be examined to clean the observation surface 80. The direction of the air or water jet applied to the observation surface 80 can be changed over a wide area by controlling the inclination of of the switching piece 6.

As is clear from this description, according to this use of the deflection system, the plate-shaped flow-course switching piece is provided in the vicinity of the outlet of the air or water supplying passage in the top metal part of the endoscope in such a manner that it can selectively project into the flow-course and be retracted therefrom. Therefore, the end face of the hollow member at the top end portion of the endoscope and the observation surface of a portion of the body under examination can be selectively cleaned. Furthermore, the entire end face of the hollow member can be cleaned by this device. In addition to the cleaning of the observation surface, it is also possible to inject a medical liquid, an anestheic liquid or a contrast medium into the diseased part of the body under observation.

Figure 14:
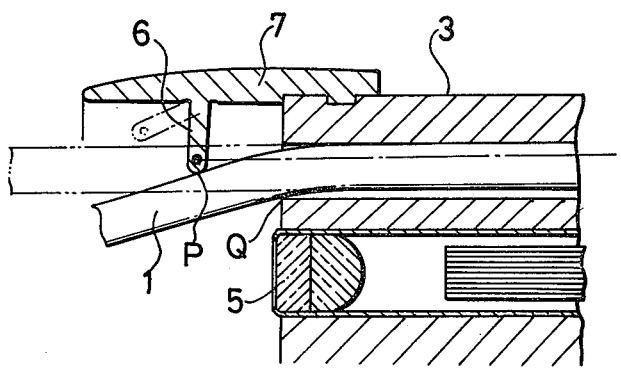
FIG. 14 is a sectional view of a third example of the second preferred embodiment of this invention.
Figure 15:
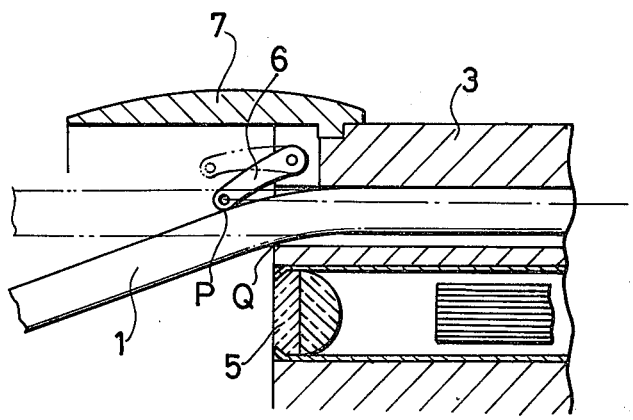
FIG. 15 is a sectional view of a fourth example of the second preferred embodiment according to this invention.

If the hood 7 is made of a hard elastic material such as synthetic resin, a flexible piece extending from the hood 7 can be employed as the depressing member 6, as in a third example of the direction changing device of the invention shown in FIG. 14. Furthermore, in the case where a depressing member 6 is arranged so that is application point P is located in the vicinity of the objective lens 5 or before the latter as shown in FIG. 15, the pivot point may be provided at the front edge of the hollow member 3.

When the depressing member 6 of the direction changing device thus constructed is not pulled with the pulling string 10 or it is retracted from the passage 2 by manually operating the pulling string 10, the inserted member 1 extending from the passage 2 pushed the depressing piece 6 aside and moves in the direction as indicated by the dotted line in FIG. 8.

When the pulling string 10 is pulled by the operation of the manual operating section of the endoscope, the depressing member 6 is rotated around the pivot shaft 70 counterclockwise as viewed in FIG. 8. As a result, the free end portion of the depressing member 6 abuts against the outer wall of the inserted member 1. Therefore, at this abutment point, point P, of application of the bending, force is applied to the inserted member and 1 and it is bent around the fulcrum Q, or the edge of the passage 2, towards the objective lens 5. If the amount of rotation of the depressing member 6, that is, the degree of bending of the inserted member 1 is controlled by operating the pulling string 10, it is possible to bring forceps or the like connected to the top end portion of the inserted member 1 to the central region of the field of vision of the objective lens 5. It is also possible to bring the forceps to any desired position in the field of vision in the central region.

Figure 19:
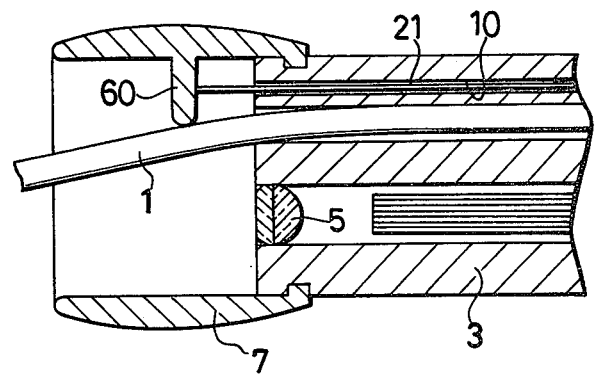
FIG. 19 is a sectional view of a variation of the second embodiment showing a separate channel for the actuating member.

A variation of the device in FIG. 14 is shown in FIG. 19, where the protrusion 60 is swung back and forth by an operating rod 10. In this case, the hood 7 and the protrusion 60 may be molded as one unit with elastic material such as synthetic resin, so that the base of the protrusion serves as the fulcrum of the aforementioned swinging motion thereof. Alternatively, the hood 7 and the protrusion 60 may be fabricated separately, so that the protrusion 60 is pivotally mounted on a predetermined part of the hood 7. Accordingly, the operating rod 10 may be a hard rod such as a wire, or a soft pulling string. The difference between the device of FIG. 14 is that a separate channel 21 is employed for the actuating member 10. This avoids any friction or tangling between the insertion member 1 and the actuating member 10.

In the remaining examples of this second preferred embodiment, the direction of the inserted member 1 is changed similarly as in the above-described example. Especially, since the point of application of the depression member 6 is located in the vicinity of the objective lens 5 or before it, the direction of the inserted member 1 can be changed without being affected by the diameter of the opening of the insertion passage 2. That is, it can be freely changed through a larger angle.

As is apparent from the above description, in the direction changing device according to this embodiment, the direction changing member is pivotally provided in the vicinity of the opening of the bioptic instrument inserting passage in the end face of the metal part provided at the top end of the endoscope. Therefore, it is unnecessary to use the internal space of the hollow member for the provision of the direction changing member. Accordingly, the internal space of the hollow member can be effectively utilized for incorporating other devices therein, whereby the arrangement around the hollow member at the top end portion of the endoscope can be miniaturized.

Because the point of application of the depressing piece is positioned in the vicinity of the end face of the metal part where the objective lens is disposed or before it, for changing the direction of the pipe, the direction of forceps or the like can be changed as desired with the opening edge of the insertion passage used as the fulcrum. In the direction changing device according to this embodiment, unlike the conventional direction changing device, it is unnecessary to widen the opening of the insertion passage in order to increase the direction changing angle, and therefore the hollow member can be more effectively utilized for other devices.

A first example of a third embodiment of the direction changing device according to this invention is shown in FIG. 16 which is a sectional view showing the essential parts of the device. In this example, an objective lens 5 of an observing optical system and an insertion passage for a bioptic instrument are provided in a hollow member 3 connected to the top end portion of an endoscope. Furthermore, well-known devices such as an irradiation optical system and a gas supplying and discharging device can be inserted in the hollow member 3. A portion of the front edge of the hollow member 3 extends along the axis of the hollow member 3 (left as viewed in FIG. 1) to form an extended wall 3a. It is further extended towards the central axis (downwardly as viewed in FIG. 16) to form a protrusion 60. The top end of the protrusion is in the movement region of an insertable member 1 of a bioptic instrument which is moved in a straight line out of the insertion passage 2. In FIG. 16, reference numeral 8 designates the image guide fiber of the optical system mentioned above, and reference numeral 7 designates a hood.

FIG. 17 is a sectional view showing the essential components of a second example of the direction changing device according to the third embodiment. In this example, the protrusion 60 is formed as a part of the hood 7. As shown, the hood has an outward tapered at its end to protect the protrusion. A third example of the direction changing device according to the invention is shown in FIG. 18. In the third example, an inwardly extending protrusion 60' is formed along the entire front edge of the hood 7. This protrusion is annular about the outer end of the hood 7 and may be of varying height. It is smaller in the vicinity of the optical member to provide a clear field of view.

In these examples, the protrusion 60 or 60' will deflect the flexible insertion member 1 towards the center of the observing optical system including the objective lens 5. However, it is preferable that the position and height of the protrusion 60 or 60' is predetermined so that the end of the member 1, being deflected, intersects the center line of the field of vision in range of 5 mm to 100 mm from the end of the encoscope, i.e., the surface of the objective lens 5.

Figure 20:
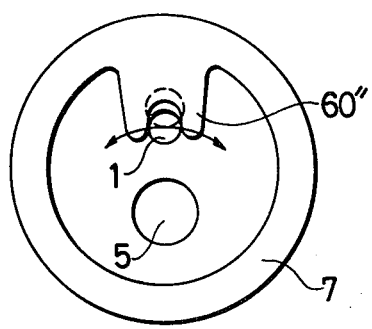
FIGS. 20-21 are end and sectional side views respectively of a fourth example of the third preferred embodiment using a clamping protrusion.
Figure 21:
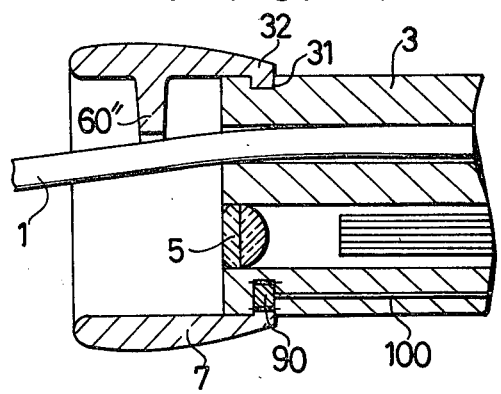

FIGS. 20 and 21 are a plan view and a sectional view showing the end portion of a fourth example of the direction changing device according to the invention, respectively. A protrusion 60" extends from a hood 7 and is formed so that it can clamp a flexible insertion member 1. The hood 7 has an engaging section which is engaged with the top end portion of an endoscope. The engaging section of the hood 7 has a gear section 90 to which a turning rod 100 is coupled. The turning rod 100 extends to a manual operating section of the endoscope.

Figure 22:
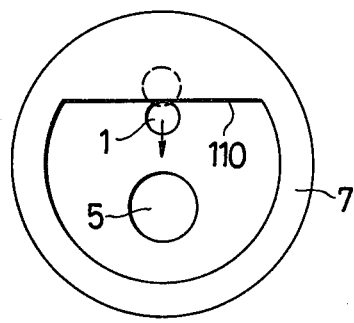
FIGS. 22-23 are end views showing the operation of a fifth example of the third preferred embodiment employing a straight bearing surface for deflecting the insertion member.
Figure 23:
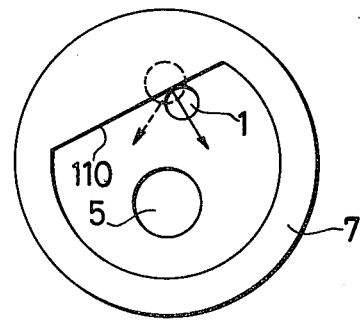

Shown in FIGS. 22 and 23 is a fifth example of the direction changing device according to the invention. In this example, the hood 7 is designed so that it is turned and positioned by manual operation as in the above-described example or directly. Furthermore, the hood 7 has a protruding bank 110 whose edge extends straight between two portions of the inner wall of the hood 7 as illustrated in the figures. In other words, the distance between the straight edge of the hood and the inner wall thereof is gradually changed.

Figure 24:
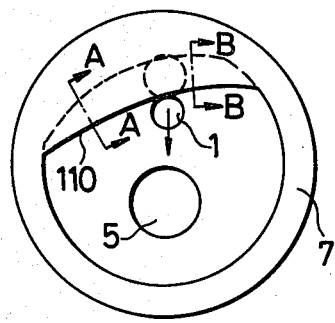
FIGS. 24-26 are end and schematic sectional views showing the operation of a sixth example of the third preferred embodiment using a tapered deflection surface.
Figure 25:
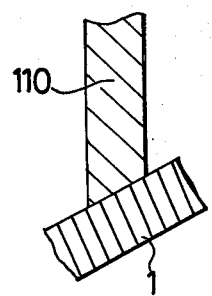
Figure 26:
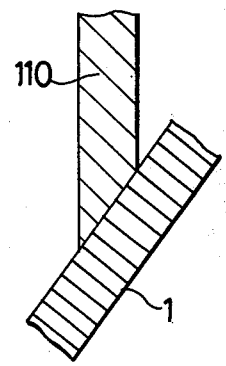

In a sixth example of the direction changing device according to the invention shown in FIGS. 24 through 26, the edge of the protrusion bearing surface 110 is curved, and the inclination of the surface of the edge, which is brought into contact with the insertion member 1, is changed as the hood is turned as shown in FIGS. 25 and 26. As shown in FIGS. 21 and 22 as the hood rotates the bearing surface the insertion member is deflected. In addition, the bank 110 is formed so that the inclination of the contact surface of the edge of the bank 110 is greatly tapered with respect to a small change of the rotation angle of the hood.

Alternatively, the hood 7 may be press-fitted to the hollow member in such a manner that the hood 7 can be turned with respect to the hollow member and can be replaced when required. The hood is also constrained from being dropped off the end of the hollow member. The hood and the hollow member have sliding surfaces, namely the groove 31 of the member and the flange 32 of the hood. In such a modification, engaging recesses are formed at suitable intervals in one of the sliding surfaces, while engaging protrusions are formed at the corresponding intervals on the other sliding surface.

The hood 7 may be made of elastic material such as synthetic resin. In this case, the engaging recesses are engaged with the engaging protrusions with the aid of the elasticity of the hood by turning the latter. In other words, the hood is designed so that it can be turned and set in one place. The drive mechanism 90,100 is eliminated.

The hood may also be made of metal material. In this case, its fitting section is so designed that it can be divided into two halves. After the two halves are fitted into the engaging groove of the hollow member 3, the hood 7 is connected directly to the fitting section made up of the two halves or it is connected to the fitting section through an intermediate member. If in this case the two halves and the intermediate member are made of elastic material, then the hood can be intermittently engaged with the metal part and positioned there by turning the hood.

Figure 27:
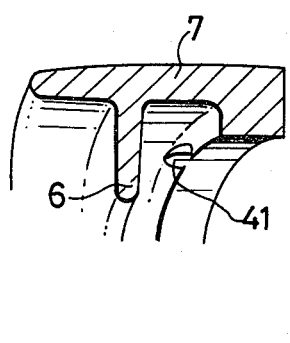
FIGS. 27 and 28 are schematic side and perspective views showing a modification of the hold rotation mechanism of FIG. 21 for selective fixed rotation of the hood.
Figure 28:
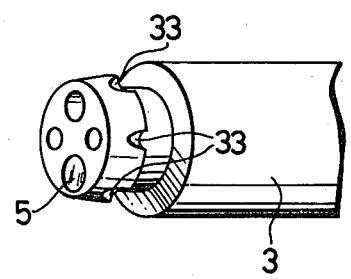

FIG. 27 is a perspective view, partly sectioned, showing the essentially components of the example of the hood according to the invention. Similarly as in the above-described example, the hood 7 has an extended protrusion 6. A plurality of small engaging protrusions 41 are provided at predetermined intervals on the rear end portion of the hood which engages with the engaging groove of the hollow member 2. A plurality of engaging recesses 33 corresponding to the small engaging protrusions 41 are formed in the wall of the engaging groove of the hollow member 2 as shown in FIG. 28.

In the above-described examples, the functioning section in the form of a protrusion extended from the inner wall of the hood and the functioning section for holding the rotation position of the hood 7 and the hollow member 2 can be combined selectively as desired. Before the device is used, the bioptic instrument extends out of the opening 2 of the insertion passage in hollow member 3 and is clamped with the forked protrusion 60 of the hood 7 which has been elastically fitted to the hollow member. Then, the hood 7 and the hollow member are held with the fingers of both hands, respectively. As was described before, the hood 7 can be turned with respect to the hollow member. The direction of the bioptic instrument clamped by the protrusion 60 as shown in FIG. 21 is changed in the direction of the arrow by turning the hood 7. When the engaging protrusion 41 of the hood 7 engages the enging recesses 33 provided in the bottom of the engaging groove of the hollow member with the direction of the bioptic instrument clamped by the protrusion 60 approaching the aimed direction, the hood is set. Thus, the hood 7 is held so that it may not readily turned with respect to the hollow member, with the bioptic instrument held in the aimed direction. If under this condition the end portion of the endoscope is inserted into a portion of the body to be examined, the observation of the portion and the operation of the bioptic instrument can be performed. This direction changing operation may be achieved by extending the bioptic instrument along the displaced protrusion 60.

If the hood is turned through a large angle, the forked protrusion 60 comes out of its working range with respect to the bioptic instrument. That is, it cannot clamp the bioptic instrument 1. Accordingly, in this case, the bioptic instrument 1 will extend straight out of the opening 2 of the passage, and therefore the bioptic instrument can be used similarly as in the case of the conventional device.

In the example shown in FIGS. 22 and 23, the protrusion can be provided in the form of a bank having the straight edge 110, which extends from the inner wall of the hood so that its abuts against the bioptic instrument. In this example also, the direction of the bioptic instrument can be changed as shown in FIG. 23 by turning the hood 7 with respect to the hollow member.

With an air or water supplying direction changing device inserted in the passage 2, when the protrusion 110 of the hood 7 is positioned so that the end portion of the protrusion 110 is above the end of the passage, the air or water elected therefrom strikes against the protrusion 110. As a result, the air or water is caused to flow toward the objective lens 5 provided in the end face of the hollow member to wash the objective lens. The rotation position of the hood 7 is maintained unchanged by the engagement of the roughened surfaces of the mating standing walls of the hood 7 and the hollow member, which serve as sliding and engaging surfaces thereof.

The mechanism for holding the hood 7 at the rotation position is not limited to the sliding and engaging surfaces of the above-described example. That is, as another example of hood, the mechanism may be formed in the surfaces of the hood 7 and the hollow member which slide on each other or come adjacent to each other when the hood 7 and the hollow member are engaged with each other.

As is apparent from the above description, in the device according to this example, the mechanism for controlling the rotation position of the hood with the protrusion acting on the bioptic instrument or acting on the supply of air or water with respect to the hollow member is provided between the hood and the tip metal part, so that the direction of extending the bioptic instrument can be changed or the direction of ejected air or water can be changed by controlling the rotation position of the hood before the endoscope is used. Accordingly, only one endoscope can be utilized for various objects, which improves the convenience in use. Furthermore, the construction of the bioptic instrument direction changing section and the air or water supplying direction changing section is very simple, and therefore the device according to this example is most effective as a mechanism employed in such an instrument whose size is extremely limited.

With the direction changing device constructed in the manner set forth in the third embodiment, the insertion member 1 is advanced in a straight line from the insertion passage and is brought into contact with the protrusion 60 in front of the objective lens 5. The member 1 is deflected towards the center region of the field of vision for observation with the opening edge of the passage acting as the fulcrum for the deflection. The deflection and deflecting angle of the pipe can be predetermined from the position (the length of the extended wall 3a or the hood 7 from the end face of the hollow member) and length of the protrusion 60. In general, the observation distance is of the order of 5 to 50 mm in the case of a bronchoscope, and it is of the order of 20 to 100 mm in the case of a gastroscope. Therefore, if the protrusion 60 or 60" is formed so that the working tip portion of the insertion member 1 intersects the center line of the field of vision for observation in this distance range, the bioptic instrument can be effectively operated under observation.

If, as shown in FIG. 19, the protrusion 60 is swung back and forth by operating the operating rod 60, the deflection of the pipe can be changed as desired, and accordingly the working end portion of the insertion member can be moved through the center of the field of vision to the opposite side of the field of vision. Thus, the pipe operating range can be greatly increased.

In the example shown in FIGS. 20 and 21, the insertion member 1 is clamped by the protrusion 60" and can be turned by turning the hood 7. Alternatively, the insertion member clamped by the protrusion 60" can be turned by turning the hood 7 while being maintained deflected towards the center of the field of vision.

In the example shown in FIGS. 22 and 23, when the pipe 1 is brought into contact with the contact surface 110 as shown in FIG. 18, member 1 is deflected towards the center of the field of vision through the largest deflecting angle. However, when the hood 7 is turned as shown in FIG. 23, the pipe 1 is moved as indicated by the solid line or the dotted line in FIG. 23, whereby the pipe is deflected in the direction (indicated by the solid line or the dotted line). In this case, it is impossible to move the working and portion of the insertion member to the center of the field of vision. However, the member 1 can be deflected in a wide area in the field of vision.

With the direction changing device shown in FIG. 23, when the insertion member is deflected by the surface 110 the portion in contact with the bank 110 is shifted from the center of the field of vision similarly as in the example shown in FIG. 22. However, in this case the inclination of the contact surface of the surface serves to shift the pipe in the direction opposite to the above-described shifting direction. Therefore, by cooperation of these elements, the deflection angle of the insertion member 1 can be varied while being directed toward the center of the field of vision.

The examples shown in FIGS. 16-18 and 20-26 can be modified to deflect a fluid stream rather than a solid flexible inserted member. As discussed with respect to FIGS. 10-14 it is sometimes necessary to inject such a fluid stream for purposes of cleaning the area under observation or the optics. Also, the device can be used for injecting dies or medicine.

Figure 29:
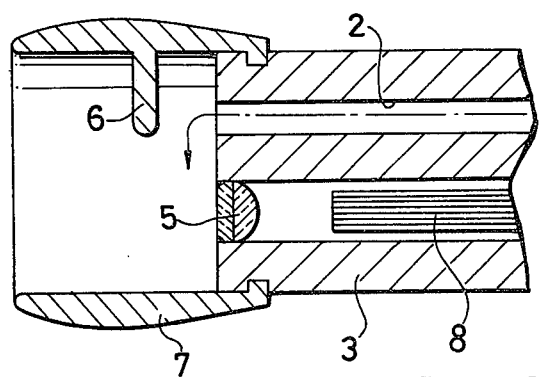
FIG. 29 is a sectional view showing the end portion of an endoscope in accordance with a first example of the fourth preferred embodiment of this invention.

Referring now to FIG. 29 a sectional view showing the end portion of an endoscope provided with a hood according to this invention is shown. An observing optical system as in the prior embodiments comprises, for instance, an objective lens 5 and a glass fiber assembly provided in elongated hollow member 3 provided at the end portion of the endoscope. A water or air supplying passage 2 is provided in parallel with the observing optical system, and has its opening in the end face of the hollow member 3. The hood 7 is fitted to the member 2 by a suitable flange and groove assembly. A protrusion 6 extends from a portion of the inner wall of the hood 7. More specifically, the protrusion 6 forming the deflection device extends towards the opening, or the outlet, of the passage 2. The end face of an irradiating light guide 8 for observation and the opening of an air or water discharging passage are provided in the end face of the hollow member 3.

Figure 30:
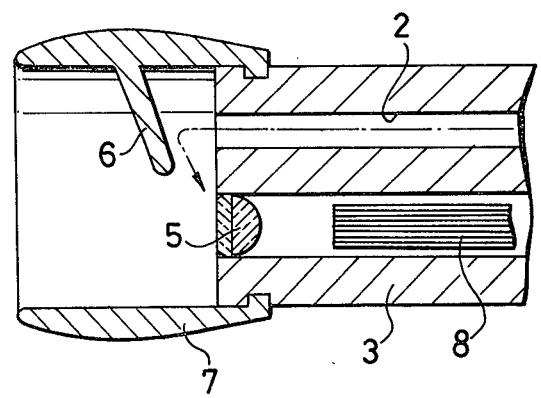
FIGS. 30-31 are sectional views showing second and third examples of the fourth preferred embodiment of this invention for the deflection of fluid.
Figure 31:
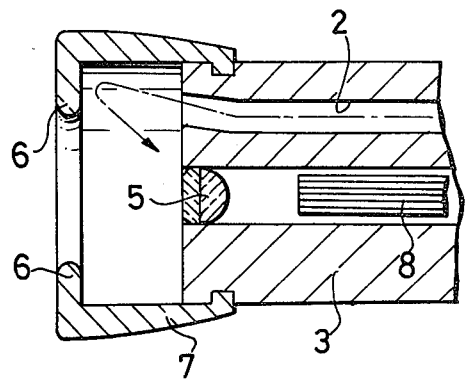

FIGS. 30 and 31 are sectional views showing the end portions of endoscopes provided with second and third examples of the hood according to this preferred embodiment, respectively. In the second example shown in FIG. 30, the protrusion 6 is directed towards the outlet of the air or water supplying passage 2, forming an acute angle with the end face of the hollow member 3. In the third example shown in FIG. 31, the protrusion 6 is in the form of an annular ring provided along the entire front edge of the hood 7. In the case of FIG. 31 the passage 2 may have a slight elevation at the outer end to direct fluid onto the protrusion device. This allows the annular ring to be relatively small and not obstruct the receiving area.

Figure 32:
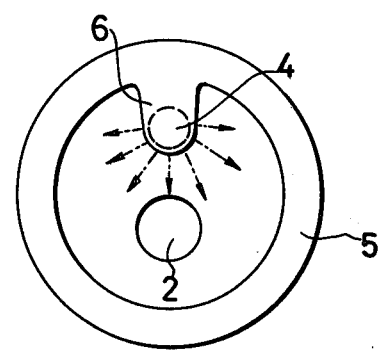
FIG. 32 is plan view of the example of FIG. 27 showing the direction dispersion of fluid.
Figure 33:
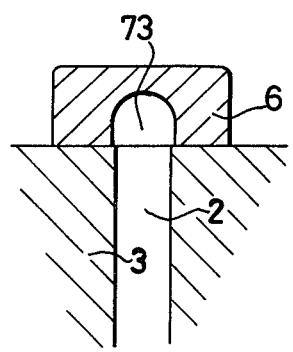
FIGS. 33-34 are sectional views showing two examples of deflecting devices according to the fourth preferred embodiment of this invention.
Figure 34:
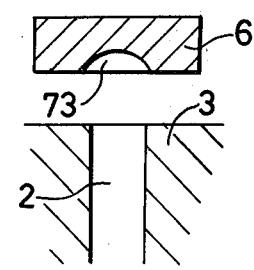

FIG. 32 is a plan view showing with arrows the direction of flow of air or water in the example of FIG. 29. FIG. 34 is a sectional view showing the configuration of the protrusion 6. As is apparent from FIG. 34, a flow-course guide groove 73 is formed in the side of the protrusion 6, which confronts the opening of the passage 2. FIG. 33 is a sectional view showing another example of the protrusion 6 in the hood according to this prepared embodiment. This protrusion 6 also has a guide groove 73, and it is designed to cover the opening of the air or water supplying passage.

If the hood 7 according to this embodiment is fitted to the end portion of the endoscope and is then positioned so that its protrusion 6 is above the opening of the air or water supplying passage 2, then the air or water supplied through the passage 2 is struck against the protrusion 6 as indicated by the arrow in FIG. 32. As a result the air or water covers the large area over the hood 7 to clean the end face of the hollow member 3 including the surface of the objective lens.

In the case where, as shown in FIG. 30, the protrusion 6 is directed towards the objective lens 5, the air or water is caused to collectively flow towards the objective lens 5. This focuses the stream onto the surface of the objective lens 1 and it is effectively cleaned. In the case where, as shown in FIG. 31, where the annular protrusion 6 is formed along the entire front edge of the hood 7, the entire front end face of the hollow member 3 of the endoscope can be cleaned. Furthermore, in this case, the annular protrusion 6 is extended toward the axis of the hood 7, that is, the front end portion of the hood 7 is bent inwardly, and therefore the annular protrusion 6 serves to prevent the entering of foreign materials such as muscous membranes of the body into the hood when the end portion of the endoscope is inserted into the body for examination.

In the situation where it is required to give greater directivity to the flow of air or water moving towards the end surface of the hollow part of the endoscope, this can effectively be fulfilled by forming the guide groove 73 in the side surface of the protrusion 6, which confronts the opening of the air or water supplying passage 2. If in this connection the protrusion 6 is formed so that the guide groove 73 covers the opening of the passage 2 as shown in FIG. 33, then the cleaning results obtained are markedly improved.

As is apparent from the above description, according to this aspect of the invention, the protrusion forming the deflection element is extended from a part of the inner wall of the hood in such a manner that the end portion of the protrusion is above the opening of the air or water supplying passage. Therefore, water or air can be positively ejected and deflected towards the end force of the hollow member of the endoscope, whereby not only the limited surface such as the surface of the objective lens but also the entire end face can be effectively cleaned. In addition, if the hood is rotated with respect to the end portion of the endoscope so that the protrusion is positioned outside the flow-course of air or water, or if the hood is removed from the end, then the jet stream of air or water can reach the observation surface of a portion of the body to be examined without being deflected by the protrusion. Hence it is possible clean the observation surface, and the passage can also be utilized for injecting a medical liquid or a contrast medium thereinto.

Figure 35:
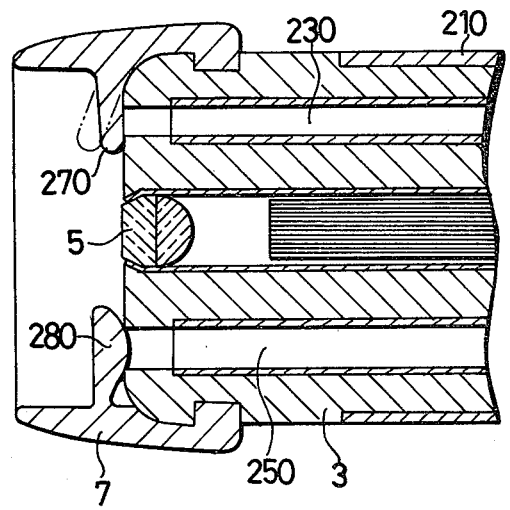
FIG. 35 is a sectional end view of a fifth embodiment of this invention employing a check valve at the opening edge.
Figure 36:
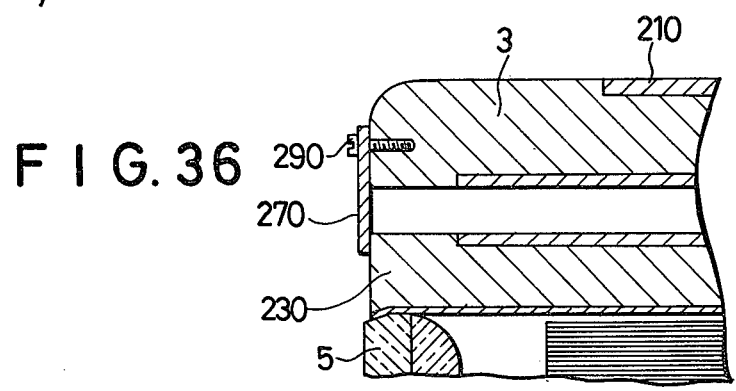
FIG. 36 is a sectional view showing a second example of the fifth embodiment of this invention.
Figure 37:
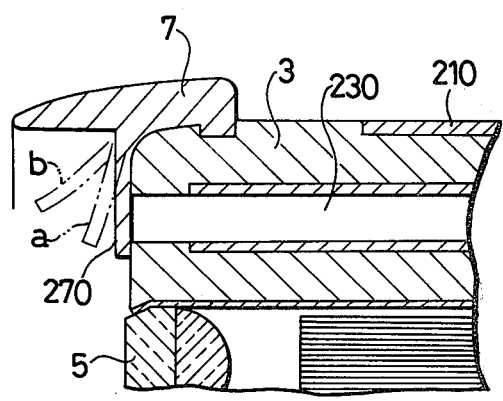
FIG. 37 is a sectional view showing a third example of the fifth embodiment of this invention.

Referring now to FIGS. 35-37 the construction of the end portion of an endoscope according to the fifth embodiment of this invention is shown. The instrument is inserted into a portion of the body to be examined, and more particularly this embodiment relates to the construction of a check valve which prevents the backward flow of body fluid or the like into the endoscope through an opening provided in the end face of hollow member connected to the end portion of the endoscope.

When then end portion of an endoscope is inserted into a portion of the body to be examined such as for instance the gullet, the stomach or the duodenum for observation, or when the internal pressure in the portion of the body to be examined is increased by the supply of air thereinto in order to maintain a distance or space between the end of the endoscope and the selected observation surface of the portion of the body, body fluid such as gastric juice or blood or residual material after digestion flows backward into the endoscope through the opening of a fluid pipe for supplying air or water or the opening of an insertion passage for forceps. Because of this backward flow of body fluid, these pipes, especially the fluid pipe, are liable to be clogged up by the residual material. Furthermore, the material brought into the pipe for forceps is pushed out to the end face of the metal part connected to the end portion of the endoscope when the forceps are used. Accordingly, the body fluid or the like thus pushed out is liable to stick on the surface of the objective lens of the observing optical system, which makes it impossible to observe the portion of the body under examination. In the case where a brush bioptic instrument is used to take a sample from a portion of the body to be examined, body fluid sticks to the brush bioptic instrument before it takes a sample therefrom, which makes it difficult to permit the brush bioptic instrument to take a large amount of good sample. If the above-described backward flow of body fluid or the like is left as it is, it is undoubtedly unsanitary, and it may cause infection among patients.

In order to overcome these difficulties, a conventional endoscope has a check valve in the vicinity of a forceps inserting opening (in a manual operating section provided at the base of the endoscope), to prevent the reduction of the internal pressure in a portion of the body to be examined and to prevent the splash of body fluid to the observer. However, since the check valve is provided in the manual operating section at the base of the endoscope, it is difficult to prevent the backward flow of body fluid or the like into the endoscope through the pipe opening at the end face of the top metal part of the endoscope when the end portion of the endoscope reaches the portion of the body to be examined. Furthermore, since the check valves greatly resists the insertion of the bioptic instrument such as forceps or a brush, it is rather difficult to allow the bioptic instrument to reach the portion of the body to be examined, and sometimes the bioptic instrument will collapse.

A first example of an endoscope according to the fifth embodiment is as shown in FIG. 35 which is a sectional view of the end portion of the endoscope. A hollow member 3 is connected to the end portion of the flexible tube 210 of the endoscope. An air or water supplying pipe 230, the objective lens 5 of an observing optical system and a pipe 250 for forceps are arranged in the hollow member 3, and have their openings in the end face of the hollow member. In FIG. 35, reference numeral 7 designates a hood press-fitted to the hollow member 3. Tongue pieces 270 and 280 extend from portions of the hood 7 towards the opening of the air or water supplying pipe 230 and the opening of the pipe 250 for forceps, respectively. The hood 7, and the tongue pieces 270 and 280 can be molded as one unit of an elastic material such as synthetic resin.

However, the tongue pieces 270 and 280 may be formed separately so that they are connected to the inner wall of the hood 6 with hinges.

Alternatively, the tongue pieces 270 and 280 made of the elastic material may be bonded to the inner wall of the hood 7. In the example shown in FIG. 35, the tongue piece 270 and the hood 7 are formed as one unit, and the degree of bending of the base of the tongue piece 270, that is, the extent of opening of the tongue piece 270 is limited so that the tongue piece cannot be swung through more than a predetermined angle with the end face of the hollow member. The base portion of the other tongue piece 280 is thinner than the remaining portion thereof so that the tongue piece 280 is swung sufficiently to open the pipe 250 for forceps.

The means for controlling the extent of bending the tongue piece 270 may be designed so that a protrusion extends from the tongue piece 270 so that it will abut against the inner wall of the hood. Alternatively, a protrusion extends from the inner wall of the hood so that is will abut against the tongue piece when the tongue piece 270 is swung to open the air or water supplying pipe 230.

FIG. 36 is a sectional view showing the essential components of a second example of the endoscope according to this embodiment. In this example, a tongue piece 270 is secured to the end face of the hollow member 3 with a screw 290. This technique may be applied to a tongue piece 270 for the pipe for forceps.

FIG. 37 is a sectional view showing the essential parts of a third example of the endoscope according to this embodiment. The tongue piece 270 is made of elastic material. The tongue piece 270 has an elastic force to close the air or water supplying pipe 230, but it can be bent to open the pipe 230 against the elastic force thereof. In the case where the tongue piece 270 is connected to the hood 7 by means of a hinge, the hinge may be provided with a spring to close the air and water supplying pipe with the tongue piece 270.

In the examples shown in FIG. 35 or 36, when the end portion of the endoscope is inserted into a portion of the body to be examined or when the pressure in the portion of the body is increased by the air or the like which has been supplied thereinto to have an observing distance therein, the tongues 270 and 280 are brought into close contact with the end face of the hollow member where the respective openings of the air or water supplying pipe 230 and the pipe 250 for forceps are provided. That is, the pipes 230 and 250 are closed by the tongue pieces 270 and 280, respectively. Hence, the tongue pieces 270 and 280 serve as check valves, and therefore the backward flow of body fluid into the pipes 230 and 250 can be positively prevented. Even if, in this case, there is a small gap between the tongue pieces 270 and 280 and the end face of the hollow member, no viscous body fluid or residual solid material will flow through the small gap into the pipes.

Since the tongue pieces 270 and 280 are bent to open the pipes by supplying air or water and pushing the forceps, air or water can be readily ejected from of the opening 230 and the forceps can be extended out of its opening 250. When the tongue piece 270 is bent to open its opening, the inside surface thereof is directed towards the objective lens 5 of the observing optical system. Therefore, the air or water ejected out of the opening of the air or water supplying pipe 230 is caused to strike against the inside surface of the tongue piece 270 thereby to flow to the observation window. As a result of which the body fluid or the like stuck to the surface of the objective lens is removed by the flow of air or water; that is, the objective lens is effectively cleaned.

In the example shown in FIG. 37 the tongue piece 270 has an elastic force to close the air or water supplying pipe. When the pressure of air or water ejected out of the air or water supplying pipe 230 is applied to the tongue piece 270, the tongue piece is bent to open the air or water supplying pipe 230. If the pressure of air or water thus ejected is relatively low, the tongue piece 270 is bent as indicated by a in FIG. 37. As a result, similarly as in the examples shown in FIGS. 35 and 36, the air or water is caused to flow to the objective lens 5. If the pressure of air or water is relatively high, the tongue piece 270 is bent as indicated by b in FIG. 37. As a result, the air or water is caused to flow substantially straightly to wash the observation surface.

As is apparent from the above description, in the device according to this embodiment, the check valves are provided on the openings of the pipe for supplying fluid such as air or water and the pipe for forceps, whereby the backward flow of body fluid into the pipes can be positively prevented during the use of the endoscope. Thus, the device according to the fifth embodiment has significant effects that the direction of flow of air or water is changed by the use of the valve to effectively clean the surface of the objective lens of the observing optical system and to selectively clean the observation surface of a portion of the body to be examined and the objective lens.

It is obvious that the endoscope according to the embodiment in which the means for preventing the backward flow of body fluid into the pipes is provided at the end portion of the endoscope is superior to the conventional endoscope in which the prevention is carried out by the manual operating section provided at the base of the endoscope. Furthermore, insertion of the bioptic instrument into a portion of the body to be examined can be readily accomplished. In addition, the arrival of the bioptic instrument to the portion of the body to be examined can be detected from the mechanical resistance which is obtained when the bioptic instrument is extended to the portion of the body after pushing aside the check valve mechanism provided on the end face of the top metal part of the endoscope. Accordingly, the careless extention of the bioptic instrument can be prevented, and therefore breaking or injuring internal walls of the body can be positively prevented. This is a secondary effect of this invention. According to the construction of the endoscope of the invention, the maintenance and replacement of the valves can be readily achieved, and the end portion of the endoscope can be readily cleaned.

What is claimed is:

1. A medical instrument for insertion into the body for the study of internal areas, comprising: an elongate hollow member having a hollow passage therein, an opening at the terminus of said passage; a member for insertion into said passage; an optical member disposed in the vicinity of said opening; means disposed adjacent said opening to deflect said insertion member to a suitable angle; said means to deflect being further operable to selectively deflect the flow of a stream of cleaning fluid from said hollow passage onto a body cavity surface or onto said optical member; a hood surrounding said opening; said means to deflect comprising a member extending beyond said opening and adapted to be positioned to deflect said insertion member; said means to deflect further comprising a pivoting deflection member having a flow directing channel to deflect said stream of fluid onto said optical member; and wherein said insertion member is adapted to deliver said stream of fluid toward said means to deflect.

2. A medical instrument for insertion into the body for the study of internal areas, comprising: an elongate hollow member having a hollow passage therein, an opening at the terminus of said passage; a member for insertion into said passage; an optical member disposed in the vicinity of said opening; means disposed adjacent said opening to deflect said insertion member to a suitable angle; said means to deflect being further operable to selectively deflect the flow of a stream of cleaning fluid from said hollow passage onto a body cavity surface or onto said optical member; a hood surrounding said opening; said means to deflect comprising a member extending beyond said opening and adapted to be positioned to deflect said insertion member; said means to deflect further comprising a pivoting deflection member having a flow directing channel to deflect said stream of fluid onto a portion of the area to be studied; and wherein said insertion member is adapted to deliver said stream of fluid toward said means to deflect.

3. A medical instrument for insertion into the body for the study of internal areas, comprising: an elongate hollow member having a hollow passage therein, an opening at the terminus of said passage; a member for insertion into said passage; an optical member disposed in the vicinity of said opening; means disposed adjacent said opening to deflect said insertion member to a suitable angle; said means to deflect being further operable to selectively deflect the flow of a stream of cleaning fluid from said hollow passage onto a body cavity surface or onto said optical member; a hood surrounding said opening; said means to deflect comprising a member extending beyond said opening and adapted to be positioned to deflect said insertion member; said means to deflect further comprising a pivoting deflection member having a first flow directing channel to deflect said stream of fluid onto said optical member and a second flow directing channel to deflect said stream of fluid onto a portion of the area to be studied; and wherein said insertion member is adapted to deliver said stream of fluid toward said means to deflect.

4. The apparatus of claim 1, 2 or 3 wherein said means to deflect is mounted for pivotal movement on said hood.

5. The apparatus of claim 4 wherein said means to deflect is mounted beyond said opening.

6. The apparatus of claim 5 further comprising a recess disposed in said hood, said means to deflect comprising a pivoting deflection member having a pivot point disposed in said recess.

7. The apparatus of claim 1, 2 or 3 wherein said means to deflect is pivotably mounted for rotation on an axis parallel to said opening edge.

* * * * *